United States Patent
Lemmens et al.

(10) Patent No.: US 7,365,195 B2
(45) Date of Patent: Apr. 29, 2008

(54) PROCESS FOR PURIFYING CAPROLACTAM

(75) Inventors: Joannes Albertus Wilhelmus J. A. W. Lemmens, Roermond (NL); Theodorus Maria T. M. Smeets, Elsloo (NL); Paul Maria P. M. Brandts, Limbricht (NL); Koen Harry Maria K. H. M. Ceyssens, Neeroeteren (BE)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 10/565,774

(22) PCT Filed: Jul. 16, 2004

(86) PCT No.: PCT/EP2004/008009

§ 371 (c)(1),
(2), (4) Date: Sep. 6, 2006

(87) PCT Pub. No.: WO2005/014538

PCT Pub. Date: Feb. 17, 2005

(65) Prior Publication Data

US 2007/0060750 A1    Mar. 15, 2007

(30) Foreign Application Priority Data

Jul. 25, 2003 (EP) .................................... 0307738

(51) Int. Cl.
*C07D 201/16* (2006.01)
(52) U.S. Cl. .................................... 540/540
(58) Field of Classification Search ................ 540/540
See application file for complete search history.

(56) References Cited

U.S. PATENT DOCUMENTS 7,141,668 B2    11/2006  Smeets et al.

FOREIGN PATENT DOCUMENTS

| EP | 0 138 241 | 4/1985 |
| EP | 0 627 417 | 12/1994 |
| EP | 0 635 487 | 1/1995 |
| GB | 1002424 | 8/1965 |
| GB | 1048193 | 11/1966 |
| GB | 2269114 | 2/1994 |

OTHER PUBLICATIONS

Lemmens et al, U.S. Appl. No. 10/557,753, filed Nov. 21, 2005.
Thomissen et al, U.S. Appl. No. 10/557,771, filed Nov. 29, 2006.
Smeets et al, U.S. Appl. No. 10/557,770, filed Nov. 21, 2005.

*Primary Examiner*—Bruck Kifle
(74) *Attorney, Agent, or Firm*—Nixon & Vanderhye P.C.

(57) ABSTRACT

The invention relates to a process for purifying caprolactam, said process comprising (a) subjecting the caprolactam to a hydrogenation by treating the caprolactam with hydrogen in the presence of a heterogeneous nickel containing hydrogenation catalyst, (b) distilling at least a portion of the hydrogenated caprolactam in a distillation column containing nickel in an amount sufficiently low such that $\Delta PAN_{Ni} \leq 3$, wherein $\Delta PAN_{Ni} = \Delta PAN - \Delta PAN_{Ni=0}$, $\Delta PAN$=increase of the PAN number of caprolactam during distilling, $\Delta PAN_{Ni=0}$ increase of the PAN number of caprolactam during distilling under the same conditions in a distillation column free of nickel. Nickel is removed from the caprolactam solution prior to the distillation step.

25 Claims, 2 Drawing Sheets

UCL-1

UCL-2

UCL-3

UCL-4

PROCESS FOR PURIFYING CAPROLACTAM

This application is the US national phase of international application PCT/EP2004/008009 filed 16 Jul. 2004 which designated the U.S. and claims benefit of EP 03077338.6, dated 25 Jul. 2003, the entire content of which is hereby incorporated by reference.

FIELD OF INVENTION

The invention relates to a process for purifying caprolactam, said process comprising (a) subjecting the caprolactam to a hydrogenation by treating the caprolactam with hydrogen in the presence of a heterogeneous nickel containing hydrogenation catalyst, and (b) distilling at least a portion of said hydrogenated caprolactam in a distillation column.

BACKGROUND AND SUMMARY OF INVENTION

Impure caprolactam, prepared by for example Beckmann rearrangement of cyclohexanone oxime, can be subjected to a number of purification steps to obtain caprolactam of the purity required for polymerisation to nylon 6. A possible purification step is the hydrogenation that can be carried out to hydrogenate unsaturated organic compounds that can be present in the impure caprolactam. The presence of these unsaturated compounds is disadvantageous because they can impair the physical-mechanical properties of the nylon-6 made by polymerizing caprolactam. The saturated organic compounds formed by hydrogenation do not adversely influence these physical-mechanical properties of the nylon-6 and moreover these compounds are more easily removed in for example a distillation following the hydrogenation.

Such a process is described in EP-A-138241. In the process as described in EP-A-138241 caprolactam is mixed with water, the so obtained aqueous caprolactam mixture is subsequently hydrogenated in the presence of a Raney nickel catalyst (example I) or a nickel on $SIO_2$ hydrogenation catalyst (example II) suspended in the aqueous caprolactam mixture to be purified. The hydrogenation catalyst is subsequently filtered off and water is removed by distillation at atmospheric pressure. The remaining product is distilled at a pressure of 0, 8 kPa and a temperature of 123° C.

It has surprisingly been found that the caprolactam obtained in such process still has a high PAN number.

The object of the invention is therefore a process for the purification of caprolactam wherein the PAN number of the obtained caprolactam is further reduced.

The object of the invention is achieved in that the distillation column contains nickel in an amount sufficiently low such that $\Delta PAN_{Ni} \leq 3$, wherein $\Delta PAN_{Ni} = \Delta PAN - \Delta PAN_{Ni=0}$, $\Delta PAN$=increase of the PAN number of caprolactam during distilling, $\Delta PAN_{Ni=0}$=increase of the PAN number of caprolactam during distilling under the same conditions but in a distillation column free of nickel.

Preferably, the amount of nickel in said distillation column is sufficiently low such that $\Delta PAN_{Ni} \leq 2$. More preferably, the amount of nickel in said distillation column is sufficiently low such that $\Delta PAN_{Ni} \leq 1$.

In a preferred embodiment, the amount of nickel in said distillation column is sufficiently low such that $\Delta PAN \leq 3$. More preferably, the amount of nickel in said distillation column is sufficiently low such that $\Delta PAN \leq 2$. Even more preferably, the amount of nickel in said distillation column is sufficiently low such that $\Delta PAN \leq 1$.

BRIEF DESCRIPTION OF THE ACCOMPANYING DRAWINGS

DETAILED DESCRIPTION OF THE PREFERRED EMBODIMENTS

Figure 1:
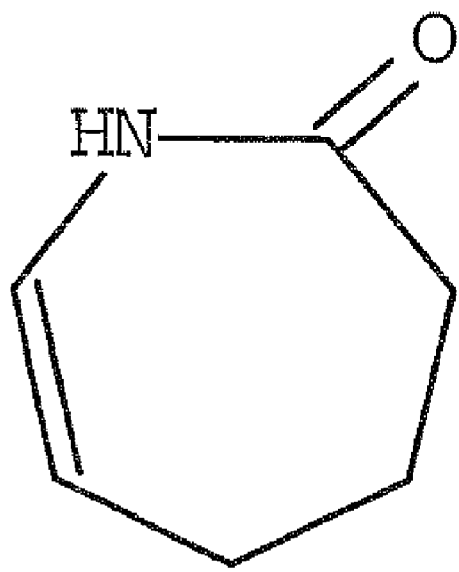
FIG. 1 depicts the structural formula of an unsaturated lactam identified as UCL-1 below.
Figure 2:
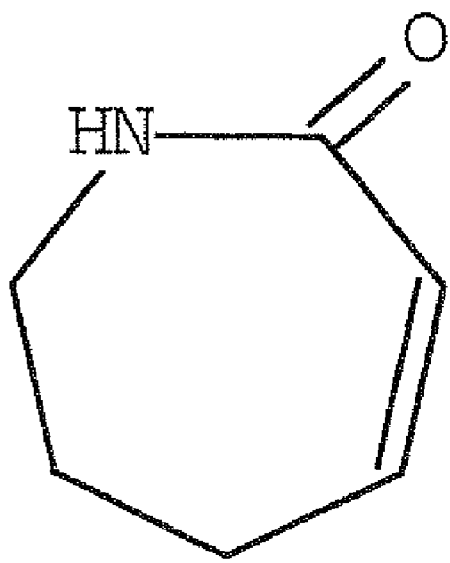
FIG. 2 depicts the structural formula of an unsaturated lactam identified as UCL-2 below.
Figure 3:
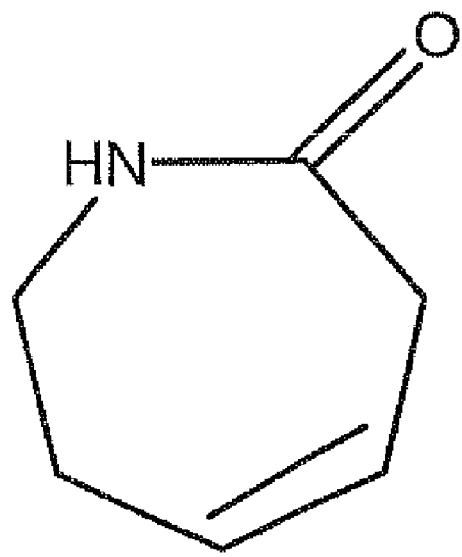
FIG. 3 depicts the structural formula of an unsaturated lactam identified as UCL-3 below.
Figure 4:
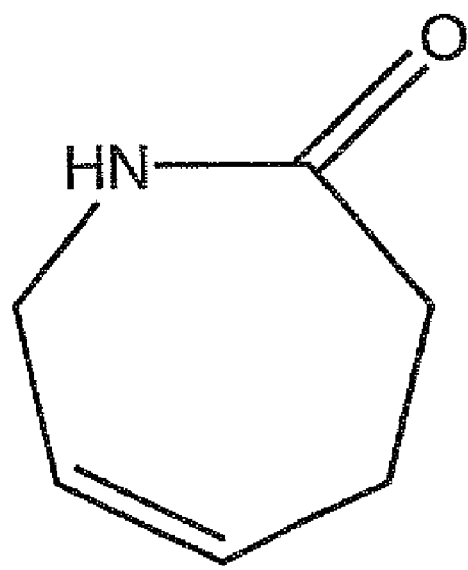
FIG. 4 depicts the structural formula of an unsaturated lactam identified as UCL-4 below.

As used herein, the increase of the PAN number of caprolactam during distilling refers to the PAN number of caprolactam leaving the distillation column minus the PAN number of caprolactam entering the distillation column. As used herein, the increase of the PAN number of caprolactam during distilling under the same conditions but in a distillation column free of nickel refers to the increase of the PAN number of caprolactam during distilling under the same conditions due to other causes than the presence of nickel in the distillation column. As used herein, the PAN number (permanganate absorption number) is determined in accordance with ISO standard 8660. The PAN number of caprolactam is a measure of the oxidizable impurities content of caprolactam. A higher PAN number means that a higher amount of oxidizable impurities is present.

The process of the present invention also relates to a process for purifying caprolactam, said process comprising (a) subjecting the caprolactam to a hydrogenation by treating the caprolactam with hydrogen in the presence of a heterogeneous nickel containing hydrogenation catalyst, (b) distilling at least a portion of the hydrogenated caprolactam in a distillation column, characterized in that the distillation column contains nickel in an amount sufficiently low such that $\Delta PAN \leq 3$, wherein $\Delta PAN$=increase of the PAN number of caprolactam during distilling. Preferably, the amount of nickel in said distillation column is sufficiently low such that $\Delta PAN \leq 2$. More preferably, the amount of nickel during said distillation column is sufficiently low such that $\Delta PAN \leq 1$.

It has surprisingly been found that the quality of the caprolactam deteriorates, in particular the PAN number increases, during said distilling in particular when having distilled high amounts of hydrogenated caprolactam. The process of the invention provides a process in which it is possible to distill a higher amount of hydrogenated caprolactam while the deterioration of the quality of caprolactam in said distilling remains the same or is even reduced.

It has surprisingly been found that reducing the amount of nickel in the distillation column results in less deterioration of the quality of caprolactam during said distilling, in particular reducing the amount of nickel in the distillation column results in that the PAN number of caprolactam during said distilling increases to a lesser extent. Reducing the amount of nickel in the distillation column to such an amount that the distillation column contains nickel in an amount sufficiently low such that $\Delta PAN_{Ni} \leq 3$ is especially advantageous in case the distilling of the hydrogenated caprolactam is performed continuously. In such continuous distillation hydrogenated caprolactam is supplied continuously to the distillation column and the distilled products are continuously withdrawn from the distillation column. In order to reduce the necessity of reducing the amount of nickel by for example cleaning the distillation column and thus in order to reduce the necessity of interruptions of a continuous distillation, it is important that high amounts can be distilled without high deterioration of the quality of the product to be distilled. The process of the present invention therefore especially relates to a process in which said distilling is performed continuously.

It has surprisingly been found that the presence of nickel in the distillation column has proved to be the cause of the deterioration of the quality of the caprolactam during said distilling inasmuch as nickel readily convert caprolactam into so-called unsaturated lactams (UCL) mainly into the compound depicted in FIG. 1 and denoted as UCL-1. Four of such unsaturated lactams with their structural formulae are depicted in FIG. 1 through FIG. 4 and denoted as UCL-1, UCL-2, UCL-3 and UCL-4, respectively. The PAN number is a measure of the oxidizable impurities content in caprolactam. The UCL's inter alia belong to the oxidizable impurities.

It was not to be expected that the quality deterioration during distilling of the hydrogenated caprolactam was caused to a large extent by the presence of nickel in the hydrogenated caprolactam fed to said distilling. It has in fact been found that, although customary techniques are applied for separating catalyst particles from the hydrogenated caprolactam, the hydrogenated caprolactam, obtained after such separation still comprises nickel. In addition, formation of unsaturated lactams may be caused by other types of chemical reactions, like for example oxidation, and/or may be caused by the presence of impurities in compounds used in the various chemical steps to produce caprolactam. Moreover, nickel is not generally known to form unsaturated lactams from caprolactam under the usually applied distillation conditions.

The hydrogenated caprolactam entering said distilling usually has a PAN number of between 2 and 5. The higher the PAN number of the hydrogenated caprolactam entering said distilling, the lower the preferred value of $\Delta PAN$.

In the process of the invention, caprolactam is subjected to a hydrogenation in the presence of a heterogeneous nickel containing catalyst. In said hydrogenation unsaturated organic compounds, which may be present in caprolactam subjected to hydrogenation, are hydrogenated. Examples of heterogeneous nickel containing catalysts are Raney nickel catalysts or supported nickel catalysts. Suitable supported nickel catalysts generally have a nickel content from 5 to 80% by weight, based on metal content and carrier. Besides nickel the catalyst may also contain activating additives such as zirconium, manganese, copper, molybdenum, iron or chromium, for example in amounts of from 1 to 20% by weight, based on the amount of nickel employed. The carriers used advantageously are alumina, silica, diatomaceous earth or activated carbon. Particularly advantageous carriers are alumina and silica.

The hydrogenation can be carried out in any way known to the person skilled in the art. In one embodiment, caprolactam is contacted with gaseous hydrogen in the presence of the catalyst. In another preferred embodiment, caprolactam is first mixed with hydrogen, for example in a static mixer, and then the mixture is brought into contact with the hydrogenation catalyst under hydrogenation conditions.

The hydrogenation may be carried out as for example a slurry phase process or with a fixed bed catalyst. In a slurry phase hydrogenation, nickel containing catalyst particles are suspended in the caprolactam to be hydrogenated. In case the hydrogenation is carried out with a fixed bed catalyst, the hydrogenation is effected in a fixed bed reactor with the catalyst being fixed in the reactor. Preferably the hydrogenation is carried out as a slurry phase process or in a fixed bed reactor with the catalyst being fixed in the reactor. In case the hydrogenation is carried out as a slurry phase process, the hydrogenation is preferably carried out in a stirred tank reactor in which the catalyst particles are suspended in the caprolactam to be hydrogenated in a pulverulent or granular form. In such slurry phase hydrogenation, the catalyst particles and the hydrogenated caprolactam are separated in an additional process step after the hydrogenation reaction step. Usually, such separation is effected by means of filtration. It has been found that, although customary separation techniques like for example filtration are applied for separating catalyst particles from the hydrogenated caprolactam, the hydrogenated caprolactam, obtained after such separation, still contains nickel. An example of a customary separation technique for separating catalyst particels from hydrogenated caprolactam is cake filtration using for example textiles woven of cotton or synthetic fibers. Another example of a customary separation technique for separating catalyst particles from hydrogenated caprolactam is using a Funda filter.

More preferably, the hydrogenation is effected in a fixed-bed reactor with the catalyst being fixed in the reactor. It has surprisingly been found that effecting the hydrogenation in a fixed-bed reactor with the catalyst being fixed in the reactor also results in the presence of nickel in the hydrogenated caprolactam. The hydrogenation is however preferably effected in a fixed-bed reactor with the catalyst being fixed in the reactor because the additional step of separating catalyst particles from the hydrogenated caprolactam can be dispensed with. An example of a possible fixed-bed reactor is the trickle-phase reactor.

The hydrogenation temperature is generally between 20 and 160° C. Within this range the reaction time can be shortened and the caprolactam quality is optimal. The temperature therefore preferably is between 60 and 130° C. The hydrogenation pressure may be between 0.1 and 3 MPa. Preferably the pressure is between 0.2 and 2 MPa. The hydrogenation can be carried out as for example described in EP-A-411455 or EP-A-635487.

Preferably, the caprolactam which is subjected to the hydrogenation is dissolved in a solvent, preferably in water. The caprolactam which is subjected to the hydrogenation preferably contains between 10 and 98 wt. % caprolactam and preferably between 2 and 90 wt. % water.

In case the hydrogenated caprolactam contains a substantial amount of water, for example more than 2 wt. % water relative to the total amount of hydrogenated caprolactam, water is preferably separated from the hydrogenated caprolactam prior to said distilling of the hydrogenated caprolactam. Separating water from the hydrogenated caprolactam may be effected in any suitable way, for example evaporating or distilling at reduced pressure.

The hydrogenated caprolactam entering said distilling may contain caprolactam, water, light components (among others unsaturated lactams) and heavy components. As used herein, light respectively heavy components are components having a boiling point lower respectively higher than the boiling point of caprolactam. Said distilling aims to recover caprolactam from the hydrogenated caprolactam. Said distilling may include separating light and/or heavy components from hydrogenated caprolactam. Said distilling is preferably performed in a vacuum distillation column. Preferably, the applied pressure at the top of the distillation column is between 0.2 and 5 kPa and the bottom temperature is preferably between 110 and 180° C. It has been found that the process of the invention is especially advantageous when said distilling of the hydrogenated caprolactam is effected in a distillation column in which the caprolactam of the hydrogenated caprolactam has a residence time of at least 5 minutes, for instance between 5 and 50 minutes. With the residence time is meant the time period between feeding the hydrogenated caprolactam comprising a certain amount of caprolactam and withdrawing that amount of caprolactam from the distillation column. More in particular, the process of the present invention is especially advantageous when distilling the hydrogenated caprolactam is effected in a distillation column having a bottom temperature of between 110 and 180° C. and in which the caprolactam of the hydrogenated caprolactam has a residence time of at least 5 minutes. An example of a distillation column in which the residence time of caprolactam is at least 5 minutes is a distillation column with sieve plates or a packing to which the hydrogenated caprolactam is fed above or on the same level as the sieve plates or packing.

The process according to the invention can be carried out in a variety of embodiments. All embodiments will aim to be able to increase the amount of hydrogenated caprolactam which can be distilled while the amount of nickel in the distillation column remains sufficiently low such that $\Delta PAN_{Ni} \leq 3$, preferably $\Delta PAN \leq 3$. To achieve this, it is preferred that the concentration of nickel in the hydrogenated caprolactam fed to said distilling should be as low as possible. The term parts per million is understood to mean the ratio consisting of grams of nickel per one million grams of caprolactam in a mixture comprising nickel and caprolactam.

In a first embodiment, the amount of nickel in the distillation column is kept sufficiently low such that $\Delta PAN_{Ni} \leq 3$, preferably $\Delta PAN \leq 3$. by cleaning the distillation column with sufficient frequency. Cleaning the distillation column is preferably effected by interrupting the distilling of the hydrogenated caprolactam, feeding an acidic solution in which nickel has a high solubility, like for example nitric acid, and rinsing the column with said acidic solution. Preferably, the acidic solution is an aqueous acidic solution.

In a second and preferred embodiment, the hydrogenated caprolactam is substantially freed (in a separate operation) of nickel prior to said distilling. In this embodiment, the process of the present invention further comprises, prior to said distilling and after said hydrogenating, separating nickel from hydrogenated caprolactam. In case of a slurry phase hydrogenation, said separating of nickel from hydrogenated caprolactam is carried out after having separated catalyst particles from the hydrogenated caprolactam and prior to said distilling. In case water is separated from the hydrogenated caprolactam prior to said distilling of the hydrogenated caprolactam, the operation to separate nickel from the hydrogenated caprolactam is preferably effected after having separated water and prior to said distilling. Separating nickel from hydrogenated caprolactam is preferably effected such that after said separating the amount of nickel in the hydrogenated caprolactam entering said distilling is less than 50 ppm, preferably less than 10 ppm, more preferably less than 1 ppm, even more preferably less than 500 ppb and even more preferably less than 100 ppb. The operation to free hydrogenated caprolactam mixture from nickel may be any operation known to one skilled in the art for removing nickel from a solution. Preferably, separating nickel from hydrogenated caprolactam is effected using filtration. An example of suitable filtration process is described in GB-A-2269114. An example of a suitable filter is a guard filter. In this embodiment of the invention, said distilling can be performed during a prolonged period of operation without having to remove nickel from the distillation column while $\Delta PAN_{Ni}$ remains lower than or equal to 3. In one embodiment, said distilling is performed continuously and $\Delta PAN_{Ni} \leq 3$, preferably $\Delta PAN \leq 3$ during a period of at least 1 month, preferably at least 2 months, more preferably at least 6 months, even more preferably at least 1 year and even more preferably at least 2 years. In another embodiment, the amount of nickel in the hydrogenated caprolactam entering said distilling is sufficiently low such that $\Delta PAN_{Ni} \leq 3$, preferably $\Delta PAN_{Ni} \leq 2$, more preferably $\Delta PAN_{Ni} \leq 1$ during a period of at least 1 month, preferably at least 2 months, more preferably at least 6 months, even more preferably at least 1 year and even more preferably at least 2 years. In this embodiment of the invention, the amount of nickel in the hydrogenated caprolactam entering said distilling is preferably less than 50 ppm, preferably less than 10 ppm, more preferably less than 1 ppm, even more preferably less than 500 ppb and even more preferably less than 100 ppb.

The invention also provides a process comprising subjecting the caprolactam to a hydrogenation by treating the caprolactam with hydrogen in the presence of a heterogeneous nickel containing hydrogenation catalyst, and distilling at least a portion of the hydrogenated caprolactam in a distillation column, wherein the amount of nickel in the hydrogenated caprolactam entering said distilling is less than 50 ppm, preferably less than 10 ppm, more preferably less than 1 ppm, even more preferably less than 500 ppb and even more preferably less than 100 ppb. This allows the distillation to be operated for a prolonged time with no or limited increase of the PAN number during distilling.

In a third and even more preferred embodiment of the invention, both the first and second embodiment are applied.

The caprolactam to be purified can be prepared by the Beckmann rearrangement of cyclohexanone oxime in oleum as for example described in DE-A-2508247 or other preparation processes, such as for instance the rearrangement reaction in the presence of an acid ion exchanger as described in GB-A-1342550. Caprolactam obtained by depolymerisation of nylon 6, as for example described in U.S. Pat. No. 5,169,870, can also be purified advantageously using the process of the present invention. It is particularly advantageous to use aqueous solutions of caprolactam obtained starting from cyclohexanone oxime, prepared by oximation of cyclohexanone with hydroxylammonium salts, by a Beckmann rearrangement of the cyclohexanone oxime in the presence of sulfuric acid or oleum, subsequent neutralisation with ammonia resulting in a solution of caprolactam in water and a solution of ammonium sulfate in water, removal of caprolactam by subjecting the neutralized rearrangement mixture or the solution of caprolactam in water to extraction with an aromatic hydrocarbon like benzene or toluene, optionally washing the obtained organic caprolactam solution with water or an aqueous alkaline solution resulting in a washed solution, and subsequent removal of the organic solvent by for example evaporation or distillation.

The invention will now be elucidated with reference to the following non-limiting examples. Nickel content was determined using Flame Absorption Atomic Spectrometry.

Comparative Experiment

At a flow rate of 90.000 kg/hour an aqueous caprolactam mixture, containing 38 wt. % caprolactam, 6 ppm UCL-1 (relative to caprolactam) and 62 wt. % water, is subjected to a hydrogenation. The hydrogenation is carried out in a reactor vessel with a total reaction volume of 15 m$^3$ with a Raney nickel catalyst concentration of 15% at a temperature of 90° C. The catalyst is suspended in the mixture to be hydrogenated by agitation. Hydrogen feed is controlled such that the hydrogen pressure is 0.5 MPa. The hydrogenation reactor effluent contains less than 2 ppm UCL-1 (relative to caprolactam) and is allowed to have a first separation by sedimentation in a vessel of 15 m$^3$ volume from which the decanted upper liquid layer is sent to a filtration unit. This filtration unit embodies a set of 2 identical cricket filters equipped with woven cotton cloth with mesh size around 15μ. Before taking a filtration unit into service a small volume of reactor effluent is being circulated over the filter during 2 hours to build up a cake layer on the filter cloth. Operation of the unit is continued until the pressure drop over the unit exceeds 300 kPa, then a back flush is carried out and the catalyst material is sent back to reactor.

Subsequently, water was removed by distillation to such an extent that the caprolactam contains 0.5 wt. % water. Subsequently, 30.000 kg/hour of this caprolactam is fed to a vacuum distillation column with a diameter of 2.5 m fitted with two beds of Mellapak 250Y packing each having a height of 4 m; caprolactam is fed at a level between the two beds of packing. The applied pressure at the bottom of the column is 3 kPa and the temperature at the bottom of the column is 160° C.

After a period of three months in operation, the increase of the PAN number of caprolactam during distilling (PAN number of caprolactam leaving the distillation column minus PAN number of caprolactam entering the distillation column) was 3.5 PAN points (ΔPAN).

EXAMPLE 1

The run was stopped and the column was flushed with 5.4 m$^3$ of a 10% nitric acid solution by circulating the nitric acid solution over the internals and reboiler of the column during a period of 4 hours. It was found that nickel had been accumulated in the column. The nickel content in the nitric acid liquid resulting from this operation was analyzed using Flame Atomic Absorption Spectrometry. From this analysis, it could be derived that 300 kg of nickel had been accumulated in the distillation column, apparently present as fouling on the internals of the column, in the sump and reboiler of the column. After having removed nickel from the distillation column, the run was continued. The increase of the PAN number of caprolactam during distilling was now zero. As in this situation the column did not contain any nickel, $\Delta PAN_{Ni=0}$ was also zero.

The performance of the filtration units was evaluated by analyzing weekly the Ni content of the caprolactam stream leaving the filtration unit. Over a period of three month the average Ni content was over 2 ppm. In the caprolactam entering the distillation column the average Ni content was 6 ppm. The Ni content was analyzed using Flame Atomic Absorption Spectrometry.

EXAMPLE 2

The run was further continued for half a year, except that the dehydrogenated, dewatered caprolactam was filtered before entering the distillation column using an additional filter unit, which was installed in front of the distillation column. The unit contains two parallel cartridges with 10μ mesh being alternately in service to ensure continuous operation. The nickel content in the caprolactam stream leaving this filtration unit was 1 ppm in average (measured with Flame Atomic Absorption Spectrometry). At the beginning of this run, the PAN number of caprolactam entering and leaving the distillation column was 2.5. During the period of half a year, the PAN number of caprolactam leaving the distillation column gradually climbed to 3.5, while during this period the PAN numbers of caprolactam entering the distillation column did not change significantly (from 2.4 to 2.6). Thus, after half a year of operation, the increase of the PAN number of caprolactam during distilling (ΔPAN) was approximately 1 point (0.9-1.1). It was decided to clean the distillation column again in an identical manner as under comparative experiment A. It turned out that 80 kg nickel had been present as fouling in the column. As $\Delta PAN_{Ni=0}=0$ (see example 1), $\Delta PAN_{Ni}$ was also approximately 1.

EXAMPLE 3

After having cleaned the distillation column, the run was further continued except that the cartridges in the filtration unit in front of the distillation column were replaced by a type of finer mesh (5μ). Nickel content in the filtrate was tracked over a period of time resulting in figures well below 1 ppm (100 ppb). During a period of 2 years operation, the PAN number of caprolactam leaving this column increases to 2.8 PAN points, while during this period the PAN numbers of caprolactam entering the distillation column did not change significantly (from 2.4 to 2.6). Thus, after 2 years of operation, the increase of the PAN number of caprolactam during distilling (ΔPAN) was approximately 0.3 points (0.2-0.4). The column was cleaned after this period in service in the same way as under Comparative Experiment A. It has been found that the nickel accumulation in the column was no more than 4 kg. As $\Delta PAN_{Ni=0}=0$ (see example 1), $\Delta PAN_{Ni}$ was also approximately 0.3.

EXAMPLE 4

After having cleaned the distillation column, the run was further continued, except that the slurry-phase hydrogenation was replaced by a fixed bed hydrogenation and a filtration unit was installed in front of the distillation column consisting of two parallel cartridges, of which one is in use, having a mesh of 5μ. The fixed-bed type catalyst was a nickel on alumina catalyst. The catalyst load to the hydrogenation reactor was 9 ton of an alumina based Ni catalyst. The nickel content is 25%, the particle size 3.2 mm. The hydrogen pressure applied is 0.5 MPa; the hydrogenation was carried out at a temperature of 90° C. The hydrogenated caprolactam leaving the fixed bed hydrogenation was subjected to the dewatering and subsequently the hydrogenated, dewatered caprolactam was fed to the distillation column. At the beginning of this run, the PAN number of caprolactam entering and leaving the distillation column was 2.5. No significant increase in PAN number of caprolactam leaving the distillation column could be detected during a period of more than 2 years in operation, while during this period the PAN numbers of caprolactam entering the distillation column did not change significantly. Incidental analysis of nickel content of the filtration unit effluent stream showed very low figures (around 10-30 ppb).

The invention claimed is:

1. Process for purifying caprolactam, said process comprising
   (a) subjecting the caprolactam to a hydrogenation by treating the caprolactam with hydrogen in the presence of a heterogeneous nickel containing hydrogenation catalyst, and
   (b) continuously distilling at least a portion of the hydrogenated caprolactam in a distillation column which contains nickel in an amount sufficiently low such that $\Delta PAN_{Ni} \leq 3$ during a period of at least 3 months, wherein $\Delta PAN_{Ni} = \Delta PAN - \Delta PAN_{Ni=0}$, $\Delta PAN$ = increase of the PAN number of caprolactam during distilling,
   $\Delta PAN_{Ni=0}$ = increase of the PAN number of caprolactam during distilling under the same conditions in a distillation column free of nickel.

2. Process according to claim 1, wherein the distillation column contains nickel in an amount sufficiently low such that $\Delta PAN \leq 3$.

3. Process according to claim 1, wherein the distillation column contains nickel in an amount sufficiently low such that $\Delta PAN_{Ni} \leq 2$.

4. Process according to claim 3, wherein the distillation column contains nickel in an amount sufficiently low such that $\Delta PAN_{Ni} \leq 1$.

5. Process according to claim 1, wherein the process further comprises, prior to said distilling, separating nickel from hydrogenated caprolactam.

6. Process according to claim 5, wherein said separating is effected using filtration.

7. Process according to claim 1, wherein the nickel containing hydrogenation catalyst is a fixed bed catalyst.

8. Process according to claim 1, wherein the hydrogenation is a slurry phase hydrogenation wherein nickel containing hydrogenation catalyst particles are suspended in the caprolactam to be hydrogenated.

9. Process according to claim 8, wherein after said hydrogenation the catalyst particles are separated from the hydrogenated caprolactam.

10. Process according to claim 5, wherein said separating of nickel from hydrogenated caprolactam is carried out after said separating of catalyst particles from the hydrogenated caprolactam.

11. Process according to claim 1, wherein the amount of nickel in the hydrogenated caprolactam entering said distilling is less than 10 ppm.

12. Process according to claim 11, wherein the amount of nickel in the hydrogenated caprolactam entering said distilling is less than 1 ppm.

13. Process according to claim 1, wherein said distilling is effected in a distillation column having a bottom temperature of between 110 and 180° C.

14. Process according to claim 1, wherein said distilling is effected in a distillation column in which the caprolactam of the hydrogenated caprolactam has a residence time higher than 5 minutes.

15. Process according to claim 1, wherein said distilling is performed continuously and $\Delta PAN_{Ni} \leq 3$ during a period of at least 6 months.

16. Process according to claim 1, wherein the amount of nickel in the hydrogenated caprolactam entering said distilling is sufficiently low such that $\Delta PAN_{Ni} \leq 3$ during a period of at least 6 months.

17. Process according to claim 1, wherein water is separated from the hydrogenated caprolactam prior to said distilling.

18. Process according to claim 1, wherein separating nickel from hydrogenated caprolactam is effected after separating of water and prior to said distilling.

19. Process according to claim 1, wherein the caprolactam entering said hydrogenation is obtained by rearrangement of cyclohexanone oxime with sulfuric acid or oleum.

20. Process for purifying caprolactam which comprises the steps of:
    (a) subjecting the caprolactam to a hydrogenation by treating the caprolactam with hydrogen in the presence of a heterogeneous nickel containing hydrogenation catalyst; and
    (b) continuously distilling at least a portion of the hydrogenated caprolactam in a distillation column which contains nickel in an amount sufficiently low such that $\Delta PAN_{Ni} \leq 3$ during a period of at least 3 months, wherein $\Delta PAN_{Ni} = \Delta PAN - \Delta PAN_{Ni=0}$, $\Delta PAN$ = increase of the PAN number of caprolactam during distilling,
    $\Delta PAN_{Ni=0}$ = increase of the PAN number of caprolactam during distilling under the same conditions in a distillation column free of nickel, and wherein
    distilling according to step (b) is continued during a period of at last 3 months, and wherein the hydrogenated caprolactam entering said distilling has a nickel content which is less than 50 ppm.

21. Process according to claim 20, wherein the nickel content in the hydrogenated caprolactam entering said distilling is less than 10 ppm.

22. Process according to claim 20, wherein the nickel content in the hydrogenated caprolactam entering said distilling is less than 1 ppm.

23. Process according to claim 20, wherein the nickel content in the hydrogenated caprolactam entering said distilling is less than 500 ppb.

24. Process according to claim 20, wherein the nickel content in the hydrogenated caprolactam entering said distilling is less than 100 ppb.

25. Process according to claim 20, wherein distilling according to step (b) is continued during a period of at least 6 months.

* * * * *